United States Patent [19]

Frost et al.

[11] Patent Number: 4,950,670
[45] Date of Patent: Aug. 21, 1990

[54] 6-PHENYL-3-(PIPERAZINYLALALKYL)-2,4(1H,3H)-PYRIMIDINEDIONE DERIVATIVES, THEIR PREPARATION AND THEIR APPLICATION IN THERAPY

[75] Inventors: Jonathan Frost, Wissous; Bernard Gaudilliere, Nanterre; Jean Rousseau, Bourg la Reine; Régis Dupont, Tours; Philippe Manoury, Verrières le Buisson; Daniel Obitz, Fontenay aux Roses, all of France

[73] Assignee: Synthelabo, Paris, France

[21] Appl. No.: 352,342

[22] Filed: May 16, 1989

[30] Foreign Application Priority Data

May 17, 1988 [FR] France ................. 88 06568

[51] Int. Cl.$^5$ ............... A61K 31/505; C07D 401/14
[52] U.S. Cl. ............................. 514/254; 514/252; 540/490; 544/91; 544/278; 544/295; 544/309; 544/363; 544/395
[58] Field of Search ............... 514/254, 252; 544/295

[56] References Cited

U.S. PATENT DOCUMENTS 4,625,028 11/1986 Smith ......................... 544/309
4,845,221 7/1989 Stack et al. ................. 544/295

OTHER PUBLICATIONS

J. Clark et al., "Heterocyclic studies. Part XIX. Some 6-(substituted phenyl)-uracil and -thiouracil derivatives", Journal of the Organic Chemical Society, vol. C. No. 10, 1971, pp. 1945-1948.
L. Strekowski et al., "Facile Preparation of 6-substituted uracils", Synthesis—Journal of Synthetic Organic Chemistry, No. 1, Jan. 1988, pp. 70-72.
M. M. Al-Arab, "Reactions off arylpropioalamides with arylacetamides", Chemical Abstracts, vol. 106, 1987, p. 650, No. 102199w.

Primary Examiner—Glennon H. Hollrah
Assistant Examiner—James H. Turnipseed
Attorney, Agent, or Firm—Wegner & Bretschneider

[57] ABSTRACT

A pyrimidinedione derivative which is a compound of formula (I):

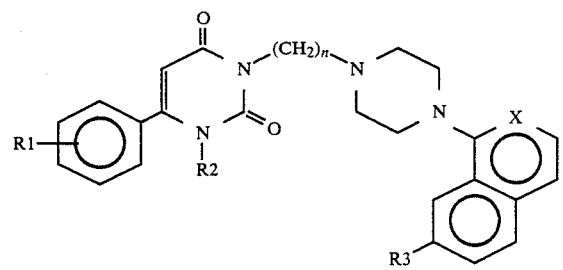

in which:
R1 denotes hydrogen, a halogen, a methyl group or a methoxy group,
R2 denotes hydrogen, a $C_1$-$C_4$ alkyl group or a benzyl group,
n denotes 2, 3 or 4,
X denotes a CH group or nitrogen, and
R3 denotes hydrogen, a halogen or a methoxy group when X denotes a CH group, with the proviso that R3 denotes hydrogen when X denotes nitrogen, or a pharmacologically acceptable acid addition salt thereof.

7 Claims, No Drawings

6-PHENYL-3-(PIPERAZINYLALALKYL)-2,4(1H,3H)-PYRIMIDINEDIONE DERIVATIVES, THEIR PREPARATION AND THEIR APPLICATION IN THERAPY

The present invention relates to 6-phenyl-3-(piperazinylalkyl)-2,4(1H,3H)-pyrimidinedione derivatives, their preparation and their application in therapy.

The present invention provides a pyrimidinedione derivative which is a compound of formula (I):

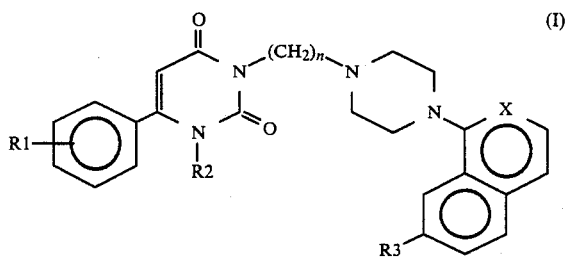

in which:
R1 denotes hydrogen, a halogen, a methyl group or a methoxy group,
R2 denotes hydrogen, a $C_1-C_4$ alkyl group or a benzyl group,
n denotes 2, 3 or 4,
X denotes a CH group or nitrogen, and
R3 denotes hydrogen, a halogen or a methoxy group when X denotes a CH group, with the proviso that
R3 denotes hydrogen when X denotes nitrogen, or a pharmacologically acceptable acid addition salt thereof.

R1 may be in the 2-,3- or 4-position on the ring to which it is attached. Examples of suitable halogens include chlorine and fluorine. Preferred groups include hydrogen; 2- or 4-F; 2- or 4-Cl; 2-,3- or 4-$CH_3$ and 4-$OCH_3$.

Examples of alkyl groups denoted by R2 include $CH_3$, $C_2H_5$ and $nC_3H_7$.

An example of a halogen denoted by X is fluorine.

The derivative of the present invention may be in the form of the free base or, for example, a hydrochloride, neutral fumarate, acid fumarate or sesquifumarate salt thereof.

The derivatives of the present invention may be prepared by the process illustrated in Scheme 1 below.

The present invention therefore provides a process for preparing a derivative as defined above wherein a compound of formula (IV) as depicted in Scheme 1 in which R1,R2 and n are as defined above is reacted with a piperazine derivative of formula (V) as depicted in Scheme 1 in which X and R3 are as defined above, and the compound of formula (I) thus obtained is, if desired, converted into a pharmacologically acceptable acid addition salt thereof.

The derivative of formula (IV) may be prepared by reacting a 6-phenyl-2,4(1H,3H)-pyrimidinedione of formula (II) as depicted in Scheme 1 in which R1 and R2 are as defined above with a dihalo derivative of formula (III) as depicted in Scheme 1 in which n is as defined above and Y denotes bromine or chlorine.

The reaction between the compounds of formulae (II) and (III) is performed, for example, in an inert solvent such as methanol or ethanol, or without a solvent other than the dihalo derivative itself, and in the presence of a phase

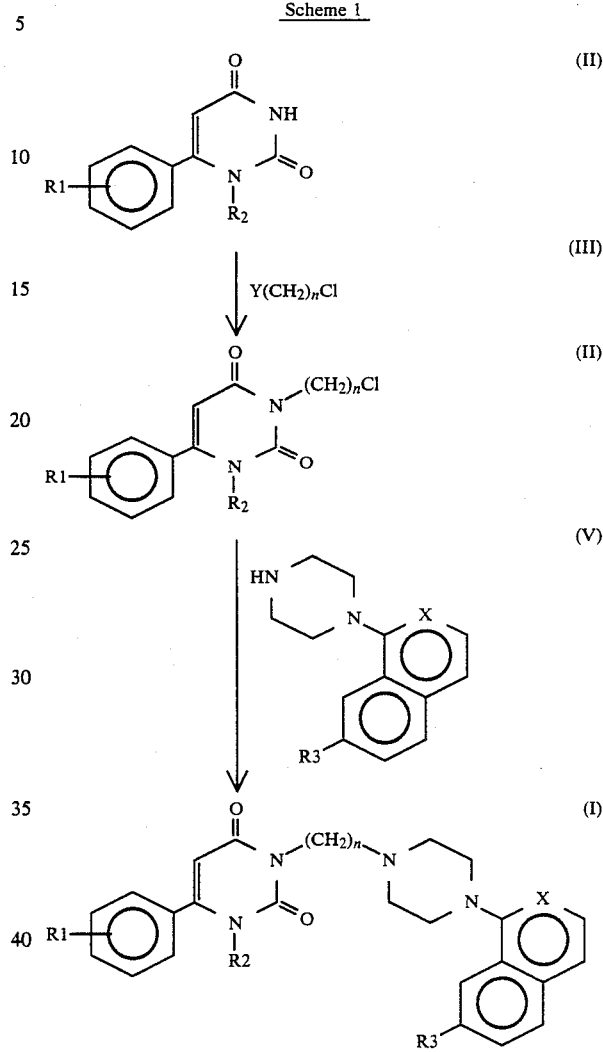

Scheme 1 transfer catalyst, for example triethylbenzylammonium chloride, in the presence of a base, for example potassium hydroxide, at reflux temperature.

The reaction between the compounds of formulae (IV) and (V) is performed, for example, in an inert solvent such as methanol or ethanol, at the refluxing temperature, or without a solvent, at a temperature of 100° to 120° C., in the presence of a base, for example an excess of the piperazine derivative of formula (V).

When R2 denotes hydrogen, enolization of the 1:2 bond of the ring of the pyrimidine of formula (II) may advantageously be turned to good account according to a variant of the process illustrated in Scheme 2 below.

The present invention therefore provides a process for preparing a derivative as defined above in which R2 denotes hydrogen wherein a bicyclic derivative of formula (IVa) as depicted in Scheme 2 in which R1 and n are as defined above, is reacted with a piperazine derivative of formula (V) as defined above, and the compound of formula (I) thus obtained is, if desired, converted into a pharmacologically acceptable acid addition salt thereof.

The derivative of formula (IVa) may be prepared by reacting a compound of formula (IIa, IIb) as depicted in Scheme 2 in which R1 is as defined above, first with an alkali metal hydride and then with a dihalo derivative of formula (III) as defined above.

The reaction between the compounds of formulae (IIa, IIb) and (III) is performed, for example, in an inert Chem., 10, 1945-1948, (1971), Synthesis, 1, 70-72, (1988) and C.A., 106, 102199w, (1987).

1-(1-Naphthyl)piperazine (general formula V, X=CH) is described in J. Med. Chem., 29 (11), 2379 (1986).

The 1-(7-R3-1-naphthyl)piperazines of formula (V) may be prepared according to the method described in this document, that is to say by reaction between a

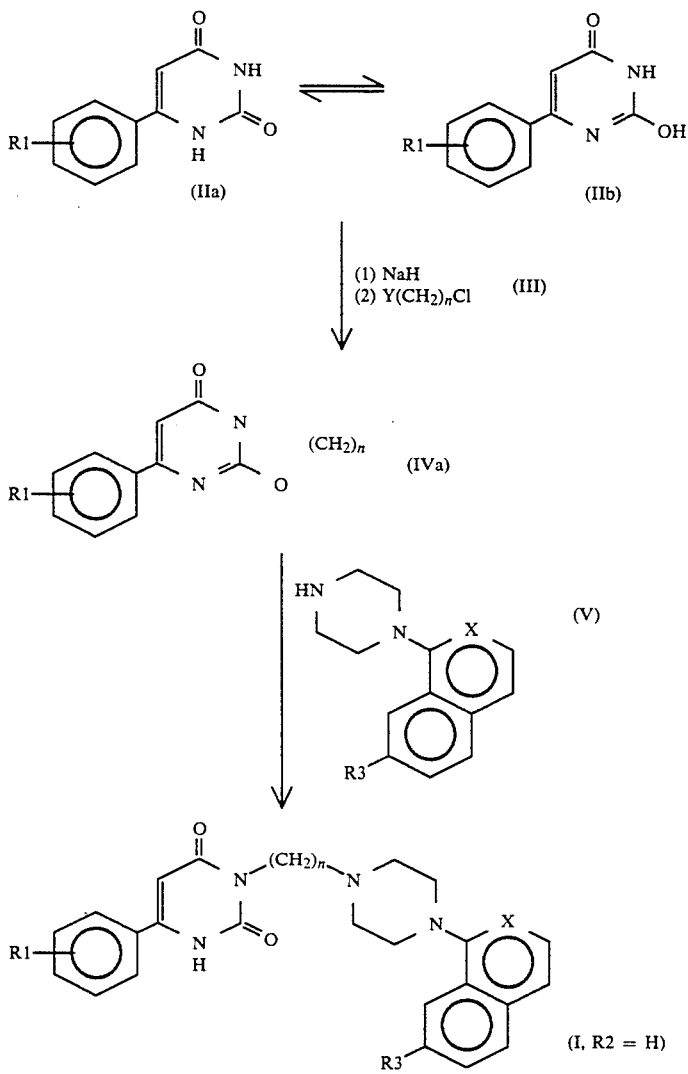

Scheme 2 solvent such as dimethylformamide.

The reaction between the compounds of formula (IVa) and (V) is performed, for example, in a solvent such as toluene, in the presence of para-toluenesulphonic acid.

The chloro derivatives of formula (IV) in which n is 2 may also be obtained by the action, for example, of thionyl chloride or methanesulphonyl chloride on the hydroxylated analogues, which are themselves obtainable from 6-phenyl-2,4(1H3H)-pyrimidinediones of formula (II) and 1,3-dioxolan-2-one.

The 6-phenyl-2,4(1H3H)-pyrimidinediones of formula (II) are described in U.S. Pat. Nos. 4,593,030, 4,652,028 and DE-A-No. 2,142,317, and in J. Org.

1-amino-7-R3-naphthalene and bis(2-chloro-2-ethyl)amine.

1-(1-Piperazinylisoquinoline) (general formula V, X=N) is new; it may be prepared in two stages, first by the action of phosphorus oxychloride on 1(2H)-isoquinolinone, and then by the action of the product thereby obtained on piperazine.

The Examples which follow further illustrate the present invention. The microanalyses and IR and NMR spectra confirm the structures of the products obtained.

The numbers shown in brackets in the titles of the Examples correspond to those in the Table given later, which illustrates the chemical structures and physical properties of some compounds of the present invention.

EXAMPLE 1 (Compound No. 4)

1-Methyl-3-{2-[4-1-naphthyl)-1-piperazinyl]ethyl}-6-phenyl-2,4(1H3H)-pyrimidinedione neutral fumarate.

(a) 3-(2-Hydroxyethyl)-1-methyl-6-phenyl-2,4(1H3H)-pyrimidinedione.

3.0 g of anhydrous potassium carbonate are added to a solution of 33.85 g (167 mmol) of 1-methyl-6-phenyl-2,4(1H3H)-pyrimidinedione and 17.0 g (193 mmol) of 1,3-dioxolan-2-one in 450 ml of dimethylformamide, and the suspension is heated under reflux for 3 h.

The mixture is allowed to cool, the inorganic product is separated off by filtration and the solvent is evaporated off under vacuum. The residue is recrystallized in 750 ml of toluene and, after drying, 35.4 g of colourless crystals are obtained.

(b) 3-(2-Chloroethyl)-1-methyl-6-phenyl-2,4(1H,3H)-pyrimidinedione.

62.5 g, equivalent to 86.1 ml (620 mmol), of triethylamine are added to a solution of 35.3 g (143 mmol) of 3-(2-hydroxyethyl)-1-methyl-6-phenyl-2,4(1H,3H)-pyrimidinedione in 1,200 ml of acetonitrile, the solution is cooled to 0° C. and, while stirring under a nitrogen atmosphere, a solution of 42.3 g, equivalent to 28.7 ml (370 mmol), of methanesulphonyl chloride in 400 ml of acetonitrile is added in such a way as to maintain the temperature below 5° C. Stirring is maintained for 3 h at this temperature, then for 1 h at 10° C. and for 1 h at 15° C.

The insoluble matter is separated off by filtration, dichloromethane and aqueous sodium bicarbonate solution are added to the filtrate and the organic phase is separated off, washed, dried and evaporated. The residue is treated by chromatography on a silica column and 17.4 g of pure product are finally obtained.

(c) 1-Methyl-3-{2-[4-(1-naphthyl)-1-piperazinyl]ethyl}-6-phenyl-2,4(1H,3H)-pyrimidinedione.

A solution of 2.2 g (8.3 mmol) of 3-(2-chloro-ethyl)-1-methyl-6-phenyl-2,4(1H,3H)-pyrimidinedione and 3.8 g (18 mmol) of 1-(1-naphthyl)piperazine in 100 ml of methanol is heated under reflux for 8 h, the solvent is then evaporated off, aqueous ammonia solution and ethyl acetate are added and the organic phase is separated off, washed with water, dried over sodium sulphate and evaporated. The oily residue is purified by chromatograph on a silica column, which leaves 2.2 g of free base. The latter is dissolved in the minimum amount of ethanol, 0.58 g of fumaric acid is added and the mixture is stirred and then left to stand.

The salt is isolated by filtration and recrystallized in ethanol. 1.80 g of fumarate are obtained.

Melting point: 158°–160° C.

EXAMPLE 2 (Compound No. 7)

3-{2-[4-(1-Naphthyl)-1-piperazinyl]ethyl}-6-phenyl-1-propyl-2,4(1H,3H)-pyrimidinedione acid fumarate.

(a) 3-(2-Chloroethyl)-6-phenyl-1-propyl-2,4(1H,3H)-pyrimidinedione.

A mixture of 9 g (39 mmol) of 6-phenyl-1-propyl-2,4(1H,3H)-pyrimidinedione, 4.36 g of potassium hydroxide, 0.43 g of triethylbenzylammonium chloride and 200 ml of 1,2-dichloroethane is heated under reflux for 1 h. The insoluble matter is separated off by filtration, the liquid phase is evaporated and the residue is purified by chromatography on a silica column, eluting with a 99:1 dichloromethane/methanol mixture. 10 g of oily product are obtained, and this is used as it is in the following stage.

(b) 3-(2-[4-(1-Naphthyl)-1-piperazinyl]ethyl}-6-phenyl-1-propyl-2,4(1H,3H)-pyrimidinedione.

A mixture of 2.92g (10 mmol) of 3-(2-chloro-ethyl)-6-phenyl-1-propyl-2,4(1H,3H)-pyrimidinedione and 4.67 g (22 mmol) of 1-(1-naphthyl)piperazine is heated on an oil bath at 120° C. for 3 h. The mixture is allowed to cool, the crystallized product is taken up with a mixture of ethyl acetate and 3N ammonia solution, the organic phase is separated off, washed with water and dried over sodium sulphate and the solvent is evaporated off. The residue oil is purified by chromatography on a silica column, eluting with a 98:2 dichloromethane/methanol mixture.

3.56 g (7.6 mmol) of base are thereby obtained, and this is dissolved in acetone, 0.88 g (7.6 mmol) of fumaric acid is added, the mixture is stirred for 1 h and the precipitate is drained and recrystallized in acetone. 2.3 g of fumarate are finally isolated.

Melting point: 182°–184° C.

EXAMPLE 3 (Compound No. 12)

1-Methyl-6-(3-methylphenyl)-3-(2-[4-(1-naphthyl)-1piperazinyl]ethyl}-2,4(1H,3H)-pyrimidinedione acid fumarate.

(a) 1-Methyl-6-(3-methylphenyl)-2,4(1H,3H)-pyrimidinedione.

A solution of 35 g (237 mmol) of N-methyl-1-(3-methylphenyl)ethanimine in 150 ml of chlorobenzene is added dropwise to 25 g, equivalent to 9.88 ml (237 mmol), of chlorocarbonyl isocyanate, and the mixture is then heated under reflux for 4 h. The solvent is evaporated off, the residue is taken up with hexane, the mixture is stirred for 3 h and filtered and the solid is purified by chromatography on a silica column, eluting with a 98:2 dichloromethane/methanol mixture. 11.9 g of product are obtained, and this is used as it is in the following stage.

(b) 3-(2-Chloroethyl)-1-methyl-6-(3-methylphenyl)-2,4(1H,3H)-pyrimidinedione.

A mixture of 11.9 g (55 mmol) of 1-methyl-6-(3-methylphenyl)-2,4(1H,3H)-pyrimidinedione, 200 ml of 1,2dichloroethane, 0.6 g of triethylbenzylammonium chloride and 6.16 g of powdered potassium hydroxide is heated under reflux for 2 h. The mixture is filtered, the filtrate is evaporated and the residual oil is purified by chromatography on a silica column, eluting with a 98:2 dichloromethane/methanol mixture. 11 g of crystallized compound are obtained.

(c) 1-Methyl-6-(3-methylphenyl)-3-{2-[4-(1-naphthyl)-1piperazinyl]ethyl}-2,4(1H,3H)-pyrimidinedione.

4.18 g (15 mmol) of 3-(2-chloroethyl)-1-methyl-6-(3-methylphenyl)-2,4(1H,3H)-pyrimidinedione and 6.79 g (32 mmol) of 1-(1-naphthyl)piperazine are mixed in a mortar. This mixture is placed in a round-bottomed flask which is heated on an oil bath at 110° C. for 3 h.

The mixture is allowed to cool, the crystallized product is taken up with a mixture of ethyl acetate and 3N ammonia solution, the organic phase is separated off, washed with water and dried over sodium sulphate and the solvent is evaporated off. The residual oil is purified by chromatography on a silica column, eluting with a 98:2 dichloromethane/methanol mixture.

5.75 g of base are thereby obtained, and this is dissolved in hot ethanol, a solution of 1.47 g of fumaric acid in the minimum amount of ethanol is added and the salt which precipitates is filtered off and recrystallized in ethanol. 5 g of fumarate are finally isolated.

Melting point: 178° C.

EXAMPLE 4 (Compound No. 15)

1-Methyl-3-{3-[4-(1-naphthyl)-1-piperazinyl]propyl}-6-phenyl-2,4(1H,3H)-pyrimidinedione hydrochloride.

(a) 3-(3-Chloropropyl)-1-methyl-6-phenyl-2,4(1H,3H)-pyrimidinedione.

A mixture of 17.5 g (86 mmol) of 1-methyl-6-phenyl-2,4(1H,3H)-pyrimidinedione, 5.7 g of potassium hydroxide and 300 ml of 1-bromo-3-chloropropane is heated under reflux for 8 h. The solvent is evaporated off, the residue is taken up with water and extracted with ethyl acetate and the organic phase is washed with water, dried over sodium sulphate and evaporated.

13 g of oily residue are obtained, and this is purified by chromatography on a silica column, eluting with a 98:2 dichloromethane/methanol mixture. 2.85 g of solid product consisting of 94% of 3-(3-chloropropyl)-1-methyl-6-phenyl-2,4(1H,3H)-pyrimidinedione, the remainder being the bromo analogue, are thereby isolated.

(b) 1-Methyl-3-{3-[4-(1-naphthyl)-1-piperazinyl]propyl}6-phenyl-2,4(1H,3H)-pyrimidinedione.

2.85 g (10.2 mmol) of 3-(3-chloropropyl)-1-methyl-6-phenyl-2,4(1H,3H)-pyrimidinedione and 5.19 g (24.5 mmol) of 1-(1-naphthyl)piperazine are mixed in a mortar. This mixture is placed in a round-bottomed flask which is heated on an oil bath at 100° C. for 1 h.

The product obtained is ground and taken up with a mixture of ethyl acetate and 3N ammonia solution, the organic phase is separated off, washed with water and dried over sodium sulphate and the solvent is evaporated off. The residue oil is purified by chromatography on a silica column, eluting with a 98:2 dichloromethane/methanol mixture. 3.4 g of base are thereby obtained, and this is dissolved in the minimum amount of acetone and ethereal hydrochloric acid is added until the pH is acid. The hydrochloride precipitates and is stirred for a further hour, and is filtered off and recrystallized in a mixture of acetone and ethanol. 1.9 g of hydrochloride are finally isolated.

Melting point: 268°–270° C. (with decomposition).

EXAMPLE 5 (Compound No. 17)

3-(2-[4-(7-Methoxy-1-naphthyl)-1-piperazinyl]ethyl)-1-methyl-6-phenyl-2,4(1H,3H)-pyrimidinedione acid fumarate.

A mixture of 1.32 g (5 mmol) of 3-(2-chloro-ethyl)-1-methyl-6-phenyl-2,4(1H,3H)-pyrimidinedione and 2.42 g (10 mmol) of 1-(7-methoxy-1-naphthyl)piperazine is heated on an oil bath for 2 h. The mixture is allowed to cool, the crystallized product is taken up with a mixture of ethyl acetate and 3N ammonia solution, the organic phase is separated off, washed with water and dried over sodium sulphate and the solvent is evaporated off. The residue oil is purified by chromatography on a silica column, eluting with a 98:2 dichloromethane/methanol mixture.

1.9 g (4 mmol) of base are thereby obtained, and this is dissolved in ethanol, 0.46 g (4 mmol) of fumaric acid are added, the mixture is stirred and the precipitate is drained and recrystrallized in ethanol. 1.64 g of fumarate are finally isolated.

Melting point: 222°–224° C.

EXAMPLE 6 (Compound No. 2)

3{2[4(7-Fluoro-1-naphthyl)-1-piperazinyl]ethyl}-6-phenyl-2,4(1H,3H)-pyrimidinedione.

(a) 1-(7-Fluoro-1-naphthyl)piperazine.

30.0 g (186 mmol) of 7-fluoro-1-naphthalenamine and 33.22 g (186 mmol) of bis(2-chloro-2-ethyl)amine hydrochloride in 170 ml of 1-butanol are introduced into a 500-ml round-bottomed flask equipped with a Dean and Stark apparatus and placed under an inert atmosphere. A little potassium iodide is added and the mixture is then heated under reflux for 20 h.

11.8 g of potassium carbonate are added, the mixture is heated under reflux for 10 h, 3.87 g of potassium carbonate are added and the mixture is heated under reflux for a further 10 h, and this latter operation is repeated twice more.

The solvent is evaporated off under reduced pressure, the residue is taken up with water and ether, the mixture is stirred, the suspension obtained is drained and the solid is recrystallized in an 80:20 water/ethanol mixture. The base is liberated from it by stirring it in water and adding sodium hydroxide, and is extracted with ether. After drying and evaporation of the organic phase, an oil is obtained which crystallizes.

Melting point: 46.5°–47.5° C.

(b) 7-Phenyl-2,3-dihydro-5H-oxazolo[3,2-a]pyrimidin-5-one.

5.65 g (30 mmol) of 6-phenyl-2,4(1H,3H)-pyrimidinedione are added in small portions to a 50% strength suspension of 1.45 g (30 mmol) of sodium hydride in oil (washed beforehand with three times 20 ml of dry pentane) in 60 ml of dry dimethylformamide, and the mixture is stirred at room temperature for 1 h until gaseous evolution ceases. The mixture is cooled in an ice bath and 7.5 ml (90 mmol) of 1-bromo-2-chloroethane are added in a single portion. The mixture is heated to approximately 70° C. for 15 h, the solvent is evaporated off and the residue is taken up with water and dichloromethane, which gives rise to a crystalline solid which is drained, washed and dried. 2.5 g of unreacted 6-phenyl-2,4(1H,3H)-pyrimidinedione are thereby recovered. Furthermore, the organic phase of the filtrate is separated off, washed and dried over magnesium sulphate, and is evaporated. 4 g of an oil are thereby obtained, and this is purified by chromatography on a silica column with a 96:4 dichloromethane/methanol mixture. After recrystallization in ether, 1.66 g of pure product are isolated. Melting point: 162°–163° C.

(c) 3-(2-[4-(7-Fluoro-1-naphthyl)-1-piperazinyl]ethyl}-6-phenyl-2,4(1H,3H)-pyrimidinedione.

1.28 g (6 mmol) of 7-phenyl-2,3-dihydro-5H-oxazolo[3,2-a]pyrimidin-5-one are mixed with 1.38 g of 1-(7-fluoro-1-naphthyl)piperazine in 25 ml of toluene in the presence of a few milligrams of para-toluenesulphonic acid, and the mixture is heated under reflux for 20 h.

The solid which has formed is drained, washed with ether and taken up with water and dichloromethane. The organic phase is washed, dried over magnesium sulphate and evaporated and the residue is stirred in boiling ethanol before being drained and dried. 1.65 g of pure product are finally isolated.

Melting point: 223°–224° C.

EXAMPLE 7 (Compound No. 25)

3-{2-[4-(1-Isoquinolyl)-4-piperazinyl]ethyl}-1-methyl-6-(2-methylphenyl)-2,4(1H,3H)-pyrimidinedione sesquifumarate.

(a) 1-(1-Piperazinyl)isoquinoline.

65 ml of phosphorus oxychloride are added dropwise to a suspension of 52.8 g (363 mmol) of 1(2H)-isoquinolinone in 250 ml of acetonitrile, the mixture is heated under reflux for 3 h and the solvent is evaporated off. The residue (305 mmol) is dissolved in methanol, a solution of 75 g (870 mmol) of piperazine in methanol is added and the solvent is evaporated off. The residue is heated to 120° C. for 4 h and allowed to cool, 500 ml of water are added, the mixture is stirred and filtered and the filtrate is extracted with ethyl acetate. After separation, washing with water, drying and evaporation of the organic phase, 57 g of base are obtained in the form of an oil.

The latter is dissolved in 400 ml of ethanol, 30.7 g of fumaric acid are added, the mixture is heated under reflux for 30 min and left to stand and the precipitate is separated off by filtration and recrystallized in a 1:1 ethanol/water mixture. 64 g of fumarate are finally isolated.

Melting point: 201°–203° C.

(b) 3-(2-Chloroethyl)-1-methyl-6-(2-methylphenyl)-2,4-(1H,3H)-pyrimidinedione.

A mixture of 10.8 g (50 mmol) of 1-methyl-6-(2-methylphenyl)-2,4(1H,3H)-pyrimidinedione, 0.5 g of triethylbenzylammonium chloride, 5.6 g of powdered potassium hydroxide and 300 ml of 1,2-dichloroethane is heated under reflux for 2 h 30 min.

The mixture is filtered, the filtrate is evaporated and the residual oil is purified by chromatography on a silica column, eluting with 98:2 dichloromethane/methanol mixture. 10.9 g of oily product are obtained, and this is used as it is in the following stage.

(c) 3-{2-[4-(1-Isoquinolyl)-4-piperazinyl]ethyl}-1-methyl-6-(2-methylphenyl)-2,4(1H,3H)-pyrimidinedione.

A mixture of 3.6 g (13 mmol) of 3-(2-chloro-ethyl)-1-methyl-6-(2-methylphenyl)-2,4(1H,3H)-pyrimidinedione and the free base obtained from 8.5 g (26 mmol) of 1-(1-piperazinyl)isoquinoline fumarate is heated on an oil bath at 120° C. for 2 h.

The mixture is allowed to cool, taken up with 3N ammonium hydroxide and extracted with three times 100 ml of ethyl acetate. The organic phase is washed, dried over sodium sulphate and evaporated. The residue oil is purified by chromatography on a silica column, eluting with 95:5 dichloromethane/methanol mixture. 5.06 g (11 mmol) of pure base are thereby obtained, and this is dissolved in ethanol, 2.76 g (22 mmol) of fumaric acid dissolved in ethanol are added and the solution is concentrated. The precipitate which forms is filtered off and recrystallized in ethanol. 5.49 g of sesquifumarate solvated with 1 mol of ethanol per mol of salt are finally isolated.

Melting point: 135°–137°.

TABLE

| No. | R1 | R2 | n | X | R3 | Salt/base | M.p. (°C.) |
|---|---|---|---|---|---|---|---|
| 1 | H | H | 2 | CH | H | base | 221–222 |
| 2 | H | H | 2 | CH | F | base | 223–224 |
| 3 | H | H | 2 | CH | OCH3 | base | 250–252 |
| 4 | H | CH3 | 2 | CH | H | fum. | 158–160 |
| 5 | H | CH3 | 2 | CH | F | base | 146–147 |
| 6 | H | C2H5 | 2 | CH | H | ac. fum. | 180–181 |
| 7 | H | nC3H7 | 2 | CH | H | ac. fum. | 182–184 |
| 8 | H | CH2C6H5 | 2 | CH | H | fum. | 162 |
| 9 | 4-F | CH3 | 2 | CH | H | base | 156–157 |
| 10 | 4-Cl | CH3 | 2 | CH | H | base | 156–158 |
| 11 | 2-CH3 | CH3 | 2 | CH | H | fum. | 196–196.5 |
| 12 | 3-CH3 | CH3 | 2 | CH | H | ac. fum. | 178 |
| 13 | 4-CH3 | CH3 | 2 | CH | H | fum. | 182–184 |
| 14 | 4-OCH3 | CH3 | 2 | CH | H | base | 132–134 |
| 15 | H | CH3 | 3 | CH | H | HCl | 268–270 |
| 16 | H | CH3 | 4 | CH | H | ac. fum. | 160 |
| 17 | H | CH3 | 2 | CH | OCH3 | ac. fum. | 222–224 |
| 18 | 2-Cl | CH3 | 2 | CH | H | fum. | 184–186 |
| 19 | 2-CH3 | CH3 | 4 | CH | H | ac. fum. | 178–180 |
| 20 | 2-F | CH3 | 2 | CH | H | fum. | 160–162 |
| 21 | H | H | 2 | N | H | base | 219–220 |
| 22 | H | CH3 | 2 | N | H | base | 138–139 |
| 23 | 4-F | CH3 | 2 | N | H | base | 136–137 |
| 24 | 4-Cl | CH3 | 2 | N | H | base | 172–174 |
| 25 | 2-CH3 | CH3 | 2 | N | H | 1½ fum.* | 135–137 |
| 26 | 4-CH3 | CH3 | 2 | N | H | fum. | 180–182 |
| 27 | 4-OCH3 | CH3 | 2 | N | H | base | 160–161 |
| 28 | H | CH3 | 4 | N | H | ac. fum. | 158 |

Key to the table
HCl: hydrochloride (base/acid = 1:1)
fum.: neutral fumarate (base/diacid = 2:1)
ac. fum.: acid fumarate (base/diacid = 1:1)
1½ fum: sesquifumarate (base/diacid = 2:3)
*solvated (salt/ethanol = 1:1)

The compounds of the invention were subjected to a series of pharmacological tests which demonstrated their value as substances having therapeutic activity.

Thus, they were subjected to a study in respect of their affinity for 5-HT$_{1A}$ serotoninergic receptors present in the rat hippocampus.

The compounds displace the binding of a labelled specific ligand, [$^3$H]-8-hydroxy-2-di-n-propylaminotetralin (hereinafter designated "[$^3$H]-8-OH-DPAT" and described by Gozlan et al, Nature, (1983), 305, 140–142) to the 5-HT$_{1A}$ receptors.

The animals used are Sprague-Dawley male rats weighing 160 to 200 g. After decapitation, their brain is removed and the hippocampus excised. The tissue is ground in an Ultra-Turrax Polytron apparatus for 30 s at half the maximum speed in 10 volumes of 50 mM Tris buffer whose pH is adjusted to 7.4 with hydrochloric acid (equivalent to 100 mg of fresh tissue per ml). The homogenized tissues are washed three times at 4° C. by centrifuging them on each occasion for 10 min at 48,000×g and resuspending the pellet in cooled fresh buffer. Finally, the last pellet is suspended in the buffer to produce a concentration of 100 mg of original tissue per ml of 50 mM buffer.

The suspension is then left to incubate a 37° C. for 10 min.

The binding with [$^3$H]-8-OH-DPAT (1 nM) is determined by incubating 100 μl of membrane suspension in a final volume of 1 ml of buffer containing 10 μM pargyline and 3 μM paroxetine.

After incubation for 15 min at 37° C., the membranes are recovered by filtration in Whatman GF/B filters, which are washed three times with 5-ml aliquot portions of ice-cold buffer. The filters are extracted in scintillation fluid and their radioactivity is measured by liquid scintigraphy. The specific binding of [$^3$H]-8-OHDPAT is defined as the quantity of radioactivity retained on the filters and capable of being inhibited by coincubation in 10 μM 5-hydroxytryptamine. At a [$^3$H]-8-OH-DAPT concentration of 1 nM, the specific binding represents 90% of the total radioactivity recovered on the filter.

For each concentration of test compounds, the percentage inhibition of the binding with [$^3$H]-8-OH-DPAT, and then the IC$_{50}$ concentration, a concentration which inhibits 50% of the binding, is determined.

For the compounds of the invention, the IC$_{50}$ values lie from 0.001 to 0.1 μM.

The compounds of the invention were also subjected to a test of displacement of the binding of spiroperidol to the serotoninergic (5-HT$_2$) receptors of the rat cerebral cortex.

For this test, the brains were removed from rats, and the cortex was dissected out and homogenized at 0° C. in 10 volumes of a mixture containing, per litre, 50 millimoles of Tris-HCl buffer, pH 7.4, 120 millimoles of sodium chloride and 5 millimoles of potassium chloride. The homogeneous mixture is centrifuged at 40,000×g for 10 min, and the pellet is then recovered, washed by being suspending in the same buffer mixture, homogenized again and centrifuged, this procedure being repeated a second time. The procedure is completed by diluting the final pellet in the same buffer mixture, in the proportion of 100 mg of wet tissue per ml of buffer.

The tissue is then subjected to a prior incubation for 10 min at 37° C. in the presence of 10 micromoles/l of pargyline, followed by an incubation for 20 minutes at 37° C. in the presence of [$^3$H]spiroperidol (specific activity: 25.6 Ci per millimole) at a concentration of 0.3 nanomole/l and of test compound at concentrations ranging from 0.0001 to 100 micromoles/l.

1 ml aliquots are withdrawn and filtered under vacuum, and the filters are washed twice with 5 ml of cold buffer and dried. The radioactivity is measured in toluene in the presence of 5 g/l of 2,5-diphenyloxazole (PPO) and 0.1 g/l of 1,4-bis(5-phenyl-2-oxazolyl)benzene (POPOP).

To assess the activity of the compounds, a curve is established for the percentage inhibition of the specific binding of [$^3$H]spiroperidol in terms of the concentration of the displacing drug. The IC$_{50}$ concentration, a concentration which inhibits 50% of the specific binding, is determined graphically.

The specific binding is defined as the binding displaced by 100 micromoles/l of 5-HT.

The IC$_{50}$ concentrations of the compounds of the invention lie, for the most part, from 0.1 to 0.5 μM.

The central activity of the compounds of the invention was assessed by their effects on the "PGO (pontogeniculooccipital) spikes" induced by reserpine (PGO-R test) in cats, according to the method described by H. Depoortere, Sleep 1976, 3rd Europ. Congr. Sleep Res., Montpellier 1976, 358–361 (Karger, Basel 1977).

Cumulative doses of test compounds are administered (from 0.001 to 3 mg/kg intravenously) at 30 min intervals, 4 h after the intraperitoneal injection of a dose of 0.75 mg/kg of reserpine, to curarized cats under artificial ventilation. The electroencephalographic and phasic (PGO-R spike) activities ar obtained using cortical and deep (lateral geniculate) electrodes. For each dose of test compound, the percentage decrease in the number of PGO spikes, and then the ED$_{50}$, the active dose which decreases this number of spikes by 50%, is determined.

For the compounds of the invention, the intravenous ED$_{50}$ values lie from 0.09 to 3 mg/kg.

Finally, the compounds of the invention were subjected to overall cerebral ischaemia test in mice. The ischaemia is due to a cardiac arrest induced by a rapid intravenous injection of magnesium chloride. In this test, the "survival time", that is to say the interval between the time of injection of magnesium chloride and the last observable respiratory movement of each mouse, is measured. This last movement is considered to be the final index of functioning of the central nervous system.

Respiratory arrest is seen approximately 19 seconds after the injection of magnesium chloride.

Male mice (Charles River CD1) are studied in groups of 10. They are supplied with food and water ad libitum before the trials. The survival time is measured 10 minutes after the intraperitoneal administration of the compounds of the invention. The results are given in the form of the difference between the survival time measured in a group of 10 mice which received the compound and the survival time measured in a group of 10 mice which received the liquid vehicle. The relationships between the modifications in the survival time and the dose of the compound are recorded graphically on a semilogarithmic curve.

This curve permits calculation of the 3-seconds effective dose (ED$_{3''}$), that is to say the dose (in mg/kg) which produces an increase of 3 seconds in the survival time relative to the control group of 10 untreated mice.

An increase of 3 seconds in the survival time is both statistically significant and reproducible.

The ED$_{3''}$ values of the best compounds of the invention (in this test) are of the order of 5 mg/kg, administered intraperitoneally.

The results of the tests show that the compounds of the present invention possess, in vitro, a high affinity and a selectivity for 5-HT$_{1A}$ type serotoninergic receptors. In vivo, they show an agonist or partial agonist activity with respect to these receptors.

The compounds of the invention may hence be used for the treatment of diseases and conditions directly or indirectly involving the 5-HT$_{1A}$ type serotoninergic receptors, in particular for the treatment of psychotic states (schizophrenia), depressive states, anxiety states, sleep disorders and disorders of sexual behaviour, and for the regulation of food intake, as well as for the treatment of vascular or cardiovascular disorders such as migraine and hypertension.

The present invention therefore also provides a compound of formula (I) or a pharmacologically acceptable acid addition salt thereof for use in a method of treatment of the human or animal body by therapy, in particular for use in the treatment of psychotic states, depressive states, anxiety states, sleep disorders, disorders of sexual behavior, regulation of food intake or vascular or cardiovascular disorders.

The present invention additionally provides the use of a compound of formula (I) or a pharmacologically acceptable acid addition salt thereof in the manufacture of a medicament for the treatment of psychotic states, depressive states, anxiety states, sleep disorders, disorders of sexual behaviour, regulation of food intake or vascular or cardiovascular disorders.

The present invention also provides a pharmaceutical composition which comprises a compound of formula (I) or a pharmacologically acceptable acid addition salt thereof and a suitable excipient.

For this purpose, they may be presented in all forms suitable for oral or parenteral administration, in combination with all suitable excipients, and in doses permitting a daily dosage of from 1 to 1,000 mg.

We claim:

1. A compound of formula:

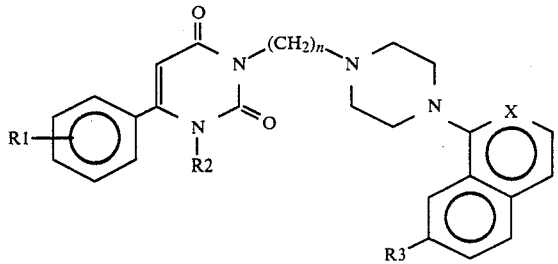

in which:
R1 denotes hydrogen, a halogen, a methyl group or a methoxy group,
R2 denotes hydrogen, a $C_1$–$C_4$ alkyl group or a benzyl group,
n denotes 2, 3 or 4,
X denotes a CH group or nitrogen, and
R3 denotes hydrogen, a halogen or a methoxy group when X denotes a CH group, with the proviso that R3 denotes hydrogen when X denotes nitrogen,
or a pharmacologically acceptable acid addition salt thereof.

2. A derivative according to claim 1 in which R1 is chlorine or fluorine.

3. A derivative according to claim 1 in which R2 is hydrogen or a methyl, ethyl or n-propyl group.

4. A derivative according to claim 1 in which R1 is fluorine.

5. A derivative according to claim 1 which is in the form of a hydrochloride, neutral fumarate, acid fumarate or sesquifumarate salt thereof.

6. A composition for the treatment of depressive states, anxiety states, vascular or cardiovascular disorders which comprises an effective amount of a compound of claim 1 and a suitable excipient.

7. A method of treatment of depressive states, anxiety states and vascular or cardiovascular disorders which comprises administering to a subject in need thereof or liable to be in need thereof an effective amount of a compound of claim 1.

* * * * *